United States Patent [19]

Penney et al.

[11] Patent Number: 5,688,771
[45] Date of Patent: Nov. 18, 1997

[54] LIPOPHILIC OLIGOPEPTIDES WITH IMMUNOMODULATING ACTIVITY

[75] Inventors: Christopher Penney, Dollard des Ormeaux; Boulos Zacharie, Laval, both of Canada

[73] Assignee: BioChem Pharma Inc., Quebec, Canada

[21] Appl. No.: 313,304
[22] PCT Filed: Apr. 2, 1993
[86] PCT No.: PCT/CA93/00144
   § 371 Date: Oct. 3, 1994
   § 102(e) Date: Oct. 3, 1994
[87] PCT Pub. No.: WO93/20100
   PCT Pub. Date: Oct. 14, 1993

Related U.S. Application Data

[63] Continuation-in-part of Ser. No. 917,464, Jul. 21, 1992, abandoned, which is a continuation-in-part of Ser. No. 862,694, Apr. 3, 1992, abandoned.

[30] Foreign Application Priority Data

Apr. 2, 1993 [WO] WIPO ............ PCT/CA93/00144

[51] Int. Cl.$^6$ .................................................. A61K 38/00
[52] U.S. Cl. ........................................ 514/19; 514/18
[58] Field of Search ............................... 514/181, 19

[56] References Cited

U.S. PATENT DOCUMENTS

| | | |
|---|---|---|
| 4,258,029 | 3/1981 | Moloney et al. |
| 5,006,515 | 4/1991 | Schwab et al. |
| 5,039,689 | 8/1991 | Daluge |

FOREIGN PATENT DOCUMENTS

| | | |
|---|---|---|
| 013856 | 8/1990 | European Pat. Off. |
| 477912 | 4/1992 | European Pat. Off. |
| WO86/03746 | 7/1986 | WIPO |
| WO90/05141 | 5/1990 | WIPO |

OTHER PUBLICATIONS

J. Freund, "The Mode of Action of Immunologic Adjuvants", *Adv. Tuberc. Res.*, 7, pp. 130–148 (1956).

S. Landi et al., "Adjuvanticity of Stearyl Tyrosine on Inactivated Poliovirus Vaccine" *Vaccine*, 4(2), pp. 99–104 (1986).

E. Lederer, "Synthetic Immunostimulants Derived from the Bacterial Cell Wall", *J. Med. Chem.*, 23, pp. 819–825 (1980).

A. Nixon et al., "Adjuvanticity of Stearyl Tyrosine on the Antibody Response to Peptide", *Viral Immunology*, 5(2), pp. 141–150 (1992).

A. Nixon–George et al., "The Adjuvant Effect of Stearyl Tyrosine on a Recombinant Subunit Hepatitis B Surface Antigen", *J. Immunol.*, 144(12), pp. 4798–4802 (1990).

M. A. Parant et al., "Immunostimulant Activities of a Lipophilic Muramyl Dipeptide Derivative and of Desmuramyl Peptidolipid Analogs", *Infection and Immunity*, 27(3), pp. 826–831 (1980).

C. L. Penney et al., "A Simple Method for the Synthesis of Long–Chain Alkyl Esters of Amino Acids", *J. Org. Chem.*, 50(9), pp. 1457–1459 (1985).

C. L. Penney et al., "Analysis of the Immunoadjuvant Octadecyl Tyrosine Hydrochloride", *Journal of Biological Standardization*, 14, pp. 345–349 (1986).

L. J. Reed et al., "A Simple Method of Estimating Fifty Per Cent Endpoints", *The American Journal of Hygiene*, 27(3), pp. 493–497 (1938).

D. F. Smee et al., "Evaluation of continuous cell lines in antiviral studies with murine cytomegalovirus", *Arch. Virol.*, 107, 253–260 (1989).

*Primary Examiner*—Avis M. Davenport
*Attorney, Agent, or Firm*—Fish & Neave; James F. Haley, Jr.; Andrew S. Marks

[57] ABSTRACT

New, small and structurally simple immunomodulating oligopeptides are disclosed. The oligopeptides of this invention possess a long, lipophilic alkyl chain. These immunomodulating oligopeptides can be used in conjunction with antiviral or anti-cancer agents in the treatment of human and animal diseases. Processes for the syntheses of immunomodulating chemicals are also disclosed.

14 Claims, No Drawings

LIPOPHILIC OLIGOPEPTIDES WITH IMMUNOMODULATING ACTIVITY

CROSS-REFERENCE TO RELATED APPLICATIONS

This application is a continuation-in-part of U.S. patent application Ser. No. 07/917,464, filed Jul. 21, 1992 (now abandoned), which is a continuation-in-part of U.S. patent application Ser. No. 07/862,694, filed Apr. 3, 1992 (now abandoned).

FIELD OF THE INVENTION

The present invention relates to immunomodulating oligopeptides which can modulate the body's immune system response to invading foreign substances and microorganisms or malignant cells.

The present invention is more particularly concerned with lipophilic desmuramyl-type peptide analogues of muramyl dipeptide and similar oligopeptides with lipophilic alkyl chains.

BACKGROUND OF THE INVENTION

Vertebrate animal immune systems are designed to protect the body from assault by parasites. These pathogens include acellular virus and cellular parasites such as bacteria, mycoplasms, fungi, unicellular protozoa and multicellular protozoa. The immune system also defends the organism against cancerous cells.

Control and fine tuning of the immune system is a goal of medical therapists. Stimulation or suppression of the immune system is often called for in the treatment or prevention of medical conditions. Control is accomplished by chemicals, such as synthetic organics, biologicals, or macromolecules from natural sources, such as glycoproteins.

Immunomodulators, thus, offer a powerful tool for the control of infectious diseases. These chemicals modulate (stimulate or suppress) the immune system in a non-specific manner. Stimulation of immunity is also important in the host*s defense against cancer. The latter occurs, for example, upon activation of tumoricidal macrophages in response to immunomodulators. Immunomodulators may also be used in the treatment of diseases caused by immune system disorders such as arthritis. They may also be used in the treatment of individuals with a compromised immune system in order to enhance their immune response. This group of patients includes surgery patients, burn victims, patients undergoing radiotherapy or chemotherapy and patients with immune disorders such as AIDS.

In general, these immunocompromised patients can be affected by viral infections such as cytomegalovirus (CMV), influenza, herpes zoster, herpes simplex, respiratory syncytial virus (RSV) and potentially hepatitis. Immunomodulators can be used to stimulate the immune system and help in fighting the viral infection. Immunomodulators can also be used as prophylactic agents in prevention of such infections.

Non-specific stimulation of the immune system also finds veterinary application as evidenced, for example, by the treatment of equine respiratory disease with a crude mycobacterial cell wall preparation.

Some immunomodulators are known in the prior art. For example, Freund's Complete Adjuvant, a water-in-oil emulsion of killed tubercle bacilli, is a well-known immunomodulator capable of increasing both the humoral and cell-mediated immune response. Its properties have been well documented for example, J. Freund, Adv. Tuberc. Res., 7, 130, 1956. However, this preparation is so toxic that its present use in humans is proscribed and its use in animals is restricted. Muramyl dipeptide (MDP; N-acetylmuramyl-L-alanyl-D-isoglutamine) is the minimal chemical structure which is both capable of replacing the mycobacterial cells present in Freund's adjuvant, while still maintaining immunomodulating activity. MDP is part of the peptidoglycan structure of bacterial cell walls. It is a unique rigid polymer which forms a net around the bacterium. MDP possesses a number of immunologic activities. For example, it is a macrophage activator and B-cell mitogen. Therefore, MDP has significant activity as an immunomodulator. MDP augments immunologic protective mechanisms against Gram negative and Gram positive bacteria, fungal parasites, viruses and tumors. MDP also produces uveitis (intraocular inflammation) in rabbits. Arthritis, an autoimmune reaction, can be produced in rats by the subcutaneous application of MDP. Muramyl dipeptide also increases the humoral response to a number of vaccines. However, MDP, like Freund's Adjuvant, is toxic. E. Lederst, in the Journal of Medicinal Chemistry, 23, 819, 1980 states that the toxic effects of MDP include pyrogenicity, transitory leukopenia, thrombocytolysis, and sensitization to endotoxin.

Numerous analogs of MDP have been synthesized and evaluated over the years in order to produce a more active and less toxic immunomodulator. It was previously believed that the carbohydrate portion of the MDP molecule was necessary for significant immunomodulating activity. However, it was thought that the carbohydrate portion could be removed if it was replaced by the addition of more amino acids or alternatively replaced by another molecular entity that was capable of interaction with receptor molecules. Such a receptor in a biological system would be any macromolecule which binds a small molecule such as MDP or a portion of such a small molecule. Upon binding of the small molecule, the macromolecule would undergo structural changes which would result in the transmission of a signal.

For example, one known compound, lauroyl tetrapeptide, replaces N-acetylmuramic acid carbohydrate. In this substitution two additional amino acids are added to the existing two, as well as a twelve carbon atom chain. FK156 adds two additional amino acids and lactic acid. "TRIGLYMYC" adds three additional amino acids, glycerol and mycolic acid. The adamantane analogs of MDP replace the carbohydrate with the antiviral agent amantidine.

However, there are problems encountered when such analogs are used. For example, they must be administered with oil in order to effectively stimulate the cell-mediated component of the immune system. Some of the known MDP analogs incorporate a long alkyl chain to make them lipophilic. The important desmuramyl peptides contain a lipophilic moiety. These moieties, such as those found in lauroyl tetrapeptide, FK156, and "TRIGLYMYC" are complex and possess varying degrees of toxicity.

More recently, several less complex MDP analogs have been synthesized. For example, L-alanyl-D-isoglutamine adamantylamide, and D,L-(2-adamantyl) glycyl-L-alanyl-D-isoglutamine are structurally simple compounds derived from the anti-viral chemical adamantans. However, they are not suitable as immunomodulating chemicals because adamantane and the drugs derived therefrom cause central nervous system side effects and congestive heart failure.

Accordingly, there is a need for compounds which have significant immunomodulating activity, are readily accessible, and possess less toxicity than the known analogs of MDP.

DESCRIPTION OF THE INVENTION

The present invention concerns novel lipophilic desmuramyl type peptide analogs of MDP and similar oligopeptides with lipophilic alkyl chains having immunomodulating activity. Thus, according to one aspect of this invention, there is provided small, structurally simple molecules which consist of an oligopeptide covalently linked to a long alkyl chain.

It has been surprisingly discovered that long alkyl chains enhance immunostimulant activity when they are covalently linked to the dipeptide portion of MDP or the oligopeptide portion of a molecule of the invention. The linkage may be effected by an ester or amide bond; by ester bond is meant any thioester and ester bond; by amide bond is meant any thioamide and amide bond.

The analogs of this invention do not replace the N-acetylmuramic acid carbohydrate with any anti-viral agents nor any small molecule which can undergo specific binding in in vivo reactions with receptors. Thus, these analogs are not chemically complex and are easy to synthesise. The structurally simple molecule which replaces muramic acid may be constructed using stearic acid. Stearic acid, stearyl alcohol (octadecanol) or other suitable long alkyl chain derivatives are non-toxic to humans. For example, stearyl alcohol has an oral LD50 of greater than 15 grams per kilogram.

Accordingly, this invention provides an oligopeptide immunomodulator of general formula (I):

Where:

Z is C=O or C=S

Y is a linker appropriate to connect an alkyl chain to the Z moiety, preferably, —O—, —S—, or —NH—; and n is an integer selected from eleven to nineteen.

HA, if present, is an organic or inorganic acid which will form a physiologically acceptable salt with the peptide, e.g., hydrochloric acid, hydrobromic acid, phosphoric acid, sulfuric acid, acetic acid, lactic acid, tartaric acid, succinic acid, citric acid, or methanesulfonic acid.

P is an oligopeptide portion comprising from 2 to 5 amino acids independently linked by amide or thioamide bonds. P is called an oligopeptide portion because it excludes its amino and acid (carboxylic or thiocarboxylic) terminal functions. The amino acids that constitute P are independently selected from naturally occurring amino acids of L-configuration or D-configuration or synthetic amino acids.

By naturally occurring amino acid is meant any amino acid, in their L or D-configuration, whether or not it is used for the build-up of proteins. Such amino acids may, for example, be selected from: alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, isoglutamine or ornithine.

Without limiting the scope of the invention, examples of synthetic amino acids may include; cyanomethylalanine and thiazolidine-4-carboxylic acid.

The invention further seeks to provide MDP analogs comprising a long alkyl chain covalently linked to a carboxyl terminus of an oligopeptide, preferably a dipeptide immunomodulator, of general formula (II):

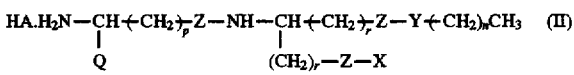

where:

is zero to four;

each Z is independently C=O or C=S;

each r is independently zero to two;

Y is a linker appropriate to connect an alkyl chain to the Z moiety, preferably, —O—, —S—, or —NH—;

n is an integer selected from eleven to nineteen; and

X is $NH_2$, OH or $OCH_3$.

HA, if present, is an organic or inorganic acid which will form a physiologically acceptable salt with the peptide, e.g., hydrochloric acid, hydrobromic acid, phosphoric acid, sulfuric acid, acetic acid, lactic acid, tartaric acid, succinic acid, citric acid, or methanesulfonic acid.

Q is $c_1$-$C_4$ branched or unbranched alkyl, phenyl, benzyl, hydroxymethyl or a side chain from any naturally occurring amino acid.

One embodiment of formula (II) is a dipeptide immunomodulator of general formula (III):

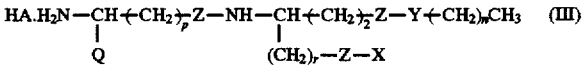

where HA, Q, P, Z, r, Y, n, and X are as defined above. Preferred embodiments of formula (III) are octadecyl L-alanyl-D-isoglutamine hydrochloride (BCH-523) and octadecyl D-alanyl-L-glutamine hydrochloride (BCH-527).

In another embodiment of formula lipophilic desmuramyl dipeptide analogs of MDP may be provided as represented by formula (IV):

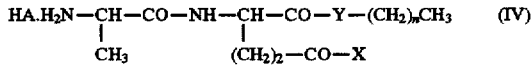

where HA, n, X, and Y, are as defined above. Both of the amino acid residues in formula (IV) are chiral. It is preferred that the alanine residue adopt the L-configuration and the second residue (for example, isoglutamine, glutamine, glutamate, etc.) adopt the D-configuration, as is observed in MDP. This does not preclude a reversal of chirality whereby, for example, the alanine residue adopts the D-configuration, and the second amino acid adopts the L-configuration. However, the two amino acids should not possess the same chirality at the alpha carbon. It will be appreciated by one of skill in the art that the MDP analog, in which both the alanine and isoglutamine amino acids possess the D-configuration, is not an immunomodulator.

Preferred oligopeptide immunomodulator of this invention are octadecyl L-alanyl D-isoglutamine, γ-octadecyl L-alanyl D-glutamate, octadecyl L-alanyl D-glutamine, α-octadecyl L-alanyl D-glutamate, octadecyl D-alanyl L-glutamine, octadecyl L-phenylglycyl D-glutamine, octadecyl D-valyl L-glutamine, octadecyl D-seryl L-glutamine, octadecyl D-phenylglycyl L-glutamine, octadecyl D-glutamate L-glutamine, octadecyl D-ornithyl L-glutamate, octadecyl L-tyrosyl glycyl glycine, and any pharmaceutically acceptable acid addition salts thereof.

Generally, synthesis of the analogs of this invention is done in two steps. The first step is to procure the desired oligopeptide. Peptides are often available from commercial suppliers. Alternatively, the desired oligopeptide may be synthesized by any conventional technique, for example, as well known in the art, by reacting amino acids in the presence of a coupling agent such as 2-ethoxy-1-ethoxycarbonyl-1,2-dihydroquinoline (EEDQ).

The second step is to react a long alkyl chain precursor, such as octadecanol or octadecyl amine, with the prepared oligopeptide. This route was used to synthesized BCH-523 in example 1.

Preferably, the analogues of this invention can be synthesized by coupling the long alkyl chain precursor with a single amino acid or an oligopeptide, followed by coupling with one or several other amino acids, to produce the desired oligopeptide immunomodulator. This route was used to synthesized BCH- 525 in example 2.

In both cases, the oligopeptide immunomodulators of formula (I) may be prepared by:

a) coupling a compound of the formula (V)

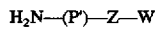

(V)

wherein:

Z is C=O or C=S;

W is an acceptable departing group such as OH, halogen, O-succinimide, triazole, imidazole, or S(E), wherein E is an $C_{1-6}$ alkyl; and P' comprises from 1 to 5 amino acids independently linked by amide or thioamide bonds; said P' excluding the amino and acid terminal functions. The amino acids are independently selected from naturally occurring, L-configuration, D-configuration or synthetic amino acids;

with a compound of the formula

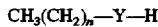

wherein n is an integer selected from eleven to nineteen and Y is an appropriate linker to connect the long alkyl chain precursor to the amino acid or oligopeptide (Y being preferably, —O—, —S—, or —NH—);

to yield a lipophilic oligopeptide of formula (VI)

(VI)

wherein P', Z, Y and n are as defined above; and b) if necessary, further coupling the amino terminal function ($H_2N$—) of said lipophilic oligopeptide of formula (VI) with the carboxylic or thiocarboxylic-terminal function (—Z—W) of a further compound of formula (V) to obtain a desired oligopeptide immunomodulator of formula (I).

Preferably, the coupling between an amino acid or an oligopeptide and an alkyl chain precursor is carried out in the presence of a coupling agent. One preferred method of alkyl chain attachment uses carbonyldiimidazole. Other suitable coupling agents include carbodiimides such as dicyclohexylcarbodiimide, diisopropyl-carbodiimide and 1-(3-dimethylaminopropyl)-3-ethylcarbodiimide.

During the preparation of the analogs of this invention, it may be preferable to temporarily protect reactive functional groups. For example, the amino terminus of the alanyl dipeptide (IV) may be protected by urethane-type groups, while the carboxyl terminus may be protected by ester groups (e.g., a benzyl ester when X is—OH). Suitable protection-deprotection conditions and protocols are described in the synthesis literature and are well known to chemists skilled in the art.

The analogs of this invention may be purified during their synthesis and/or after their preparation by standard techniques well known to the skilled artisan. One preferred purification technique is silica gel chromatography. In particular, the flash chromatographic technique may be used. However, other chromatographic methods, including HPLC, may be used for purification of the product analogs. Crystallization may also be used to purify the products, as may washing procedures with appropriate organic solvents.

The oligopeptides of the invention generally possess limited solubility in physiologically milieu; such as physiological (0.9%) saline, or phosphate buffered saline (PBS). Thus, for example, it is generally observed that when X is —$NH_2$, in formula II, (as in isoglutamine, glutamine), the solubility is limited. It is generally less than 0.01 mg/mL. If the analogs are insoluble in an aqueous medium, they should be capable of forming microparticles having a size of between about 150 µM-1 mM (mesh 18-mesh 100), thereby giving rise to a suspension of uniform consistency. A preferred formulation employs aqueous suspensions of mesh 60 material, or particles of approximately 250 µM diameter.

The invention also concerns method for the treatment or prophylaxis of viral infection in a mammal. By mammal is meant any of a class of higher vertebrates comprising human. Without limiting the scope of the invention, viral infection may be selected from the group consisting of cytomegalovirus (CMV), influenza, herpes zoster, herpes simplex, respiratory syncytial virus (RSV) and hepatitis.

The analogs of the invention described by the above formulas may be formulated using techniques similar to those employed for other pharmaceutical peptide compositions. Thus, the analogs may be stored in lyophilised form, or as a dry powder, and reconstituted in a physiologically acceptable vehicle to form a suspension or solution prior to administration. Alternatively, the analogs may be stored in the treatment vehicle. Preferred vehicles are sterile solutions, in particular, sterile buffer solutions, such as phosphate buffered saline. The vehicle may contain preservatives or other known additives which are used to improve the shelf stability or the efficacy of the mixture. Such preservatives include, for example, thimerosal or phenoxyethanol.

While it may be possible that, for use in therapy, an oligopeptide of the invention may be administered as the raw chemical, it is preferable to present the active ingredient as a pharmaceutical formulation.

The invention thus further provides a pharmaceutical formulation comprising the oligopeptides of formulas (I)–(IV) or a pharmaceutically acceptable acid addition salt thereof together with one or more pharmaceutically acceptable carriers therefor and, optionally, other therapeutic and/or prophylactic ingredients. The carrier(s) must be "acceptable" in the sense of being compatible with the other ingredients of the formulation and not deleterious to the recipient thereof.

Pharmaceutical formulations include those suitable for oral, rectal, nasal, topical (including buccal and sub-lingual), vaginal or parenteral (including intramuscular, subcutaneous, intravenous and intra-peritoneal) administration or in a form suitable for administration by inhalation or insufflation. The formulations may, where appropriate, be conveniently presented in discrete dosage units and may be prepared by any of the methods well known in the art of pharmacy. All methods include the step of bringing into association the active compound with liquid carriers or finely divided solid carriers or both and then, if necessary, shaping the product into the desired formulation.

When desired, the above described formulations adapted to give sustained release of the active ingredient, may be employed.

Immunomodulators of the invention can be used in conjunction with other pharmaceutically active therapeutic agents. Such a combination can be synergistic or the combined agents can simultaneously affect multiple problems. Without necessarily restricting the scope of the invention, several examples are envisaged.

One example comprises the immunomodulators of the invention and an anticancer compound, such as antimetabolites, intercalating agents, mitotic inhibitors, alkylating agents or other cytotoxic inhibitors such as cisplatin.

The immunomodulators of the invention can also be used with immunotoxins monoclonal or polyclonal antibodies, or cytotoxic cells such as lymphokine activated killer cells or tumor infiltrating lymphocytes among others.

The immunomodulators of the invention may also be administered together with antiviral agents. Some antiviral chemicals may work well with the immunomodulators of this invention. These may be selected from such agents as acyclovir, ganciclovir ribavirin, amantidine, azidothymidine, foscarnet, 2'-deoxy-3'-thiacytidine (3TC), 2'3'-dideoxycytidine (ddC), 2'3'-dideoxyinosine (ddI), 2'3'-dideoxyadenosine (ddA), 5'-iododeoxyuridine, and Carbovir. Other suitable antiviral chemicals could conceivably be used in combination with the immunomodulators of this invention. Such antiviral chemicals are well known to chemists skilled in the art. Such antiviral agents could conceivably be used in the treatment of AIDS, hepatitis, CMV and other virus diseases, in conjunction with the immunomodulators of this invention.

In addition, the immunomodulators of this invention may also be used in combination with antibacterial antibiotics, antifungal drugs, antiprotozoal drugs or other antimicrobials.

Preferably a dosage level of 0.1 to 1000 mg/kg of body weight of the analog chemical of the invention, is administered for mammals. A more preferred amount of analog is 10 to 500 mg/kg of body weight. The dosage will depend upon the host receiving the compound as well as factors such as the size, weight, and age of the host.

The immunomodulators of this invention were tested using four different methods. The first method is exemplified in detail in example 22 and in Table 1. The method consists of a plaque-forming assay using spleen cells from mice that were challenged with sheep red blood cells and injected with an immunomodulator of this invention. Subsequently the harvested spleen cells were incubated with fresh sheep red blood cells and guinea pig complement in a Cunningham chamber. Areas of hemolysis were counted, as they were indicative of plaque-forming cells. Table 1 shows the results of the immunomodulating activity of some selected examples of the oligopeptides of this invention.

The following oligopeptides of this invention have been found to be immunostimulants: octadecyl L-alanyl D-isoglutamine (BCH-523); octadecyl L-alanyl D-glutamine (BCH-525); octadecyl D-alanyl L-glutamine (BCH-527); octadecyl L-alanyl D-glutamyl glycine (BCH-1315); L-alanyl D-isoglutamyl octadecylamine (BCH-1316); and octadecyl L-tyrosyl glycyl glycine (BCH-276).

The following oligopeptides of this invention were found to be immunosuppressors: octadecyl L-alanyl D-glutamate (BCH-524 and BCH-526) and octadecyl D-ornithyl L-glutamate (BCH-1325).

The second method for testing immunomodulators of this invention is described in detail in examples 23 and 24. Mice were administered a 50 mg/kg dose of the immunomodulators of the invention and were subsequently sacrificed. The spleens were harvested and splenocytes isolated. Immunologic assays were conducted on those splenocytes that were taken 24 hours after final treatment. These cells were subjected to tests to determine macrophage and natural killer (NK) cell function. Splenic cell B and T cell counts were also conducted and, in summary, are as follows.

The following immunomodulators caused macrophage stimulation: octadecyl L-alanyl D-isoglutamine (BCH-523); γ-octadecyl L-alanyl D-glutamate (BCH-524); and octadecyl D-alanyl L-glutamine (BCH-527). Octadecyl L-alanyl D-glutamine (BCH-525) and α-octadecyl L-alanyl D-glutamate (BCH-526) caused moderate macrophage suppression. Natural Killer (NK) cell activity was stimulated by octadecyl D-alanyl L-glutamine (BCH-527). γ-Octadecyl L-alanyl D-glutamate (BCH-524) and octadecyl L-alanyl D-glutamine (BCH-525) gave marginal natural killer cell suppression.

γ-Octadecyl L-alanyl D-glutamate (BCH-524) suppressed both B and T cells. α-Octadecyl L-alanyl D- glutamate (BCH-526) and octadecyl D-alanyl L-glutamine (BCH-527) increased B cell counts and suppressed T cell counts.

The third method is exemplified in detail in example 25 and in tables 5–6. This method is very similar to the second one. The activity of the natural killer cells (NK) was determined and a macrophage function assay was done. In this case a proportion of the mice population was infected with influenza A/NWS/33 prior to this determination. Doses varying from 0 to 200 mg/kg of an immunomodulator of the invention were administered. Octadecyl L-alanyl D-glutamine (BCH-527) causes a macrophage stimulation and stimulated the natural killer cells activity.

The fourth method is exemplified in detail in example 26 and in tables 7–8–9. The method consist of the prophylactic treatment with an immunomodulator of this invention, of mice later challenged with CMV. The death ratio was observed and the virus titers of different organs was calculated. Octadecyl D-alanyl L-glutamine (BCH-527) was found to have a prophylactic activity by preventing death and reducing tissue virus titres.

EXAMPLE 1

Synthesis of Octadecyl L-Alanyl-D-Isoglutamine Hydrochloride (BCH-523)

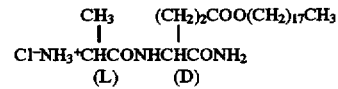

1.1 g, 7 mmole carbonyldiimidazole was added to BOC L-alanyl D-isoglutamine (1.9 g, 6 mmoles of the free acid), dissolved in 50 mL dry tetrahydrofuran, and stirred under argon flow. The solution was allowed to stir for 45 minutes at ambient temperature and then octadecanol (2.0 g, 7.2 mmole) was added under continued argon flow. The reaction was stirred at ambient temperature and under argon for twenty hours. Removal of the solvent by rotary evaporation gave 4.9 g of crude product. The solid was solubilized in 50 mL of chloroform and the solution was extracted with 0.5N hydrochloric acid (3×40 mL), 5% sodium bicarbonate (2×50 mL), and water (50 mL). The organic phase was then dried with anhydrous sodium sulphate. Removal of the solvent gave 2.7 g, of solid. The octadecyl ester of BOC L-alanyl D-isoglutamine was purified from this solid by flash silica gel chromatography. The column was eluted respectively with 1:1 hexane/methylene chloride, methylene chloride, and methylene chloride/methanol (1%, 5% and finally 10% v/v of the latter solvent). Yield of the product was 1.2 g. The product was identified by 300 RHz NMR spectroscopy and TLC. Removal of the BOC protecting group was undertaken by solubilization of the product in methylene chloride followed by bubbling hydrogen chloride gas through the solution for 10 minutes at room temperature. The hazy solution was stored at 4° C. for two hours and filtered, and the solid chemical dried in vacuo. The yield of white hydrochloride salt of octadecyl L-alanyl D-isoglutamine was 1.0 g. This gave a 33% yield from the BOC dipeptide reactant. The final product was confirmed by 300 MHz NMR spectroscopy and TLC (iodine and ninhydrin positive). The final product may be washed with acetone and/or ether.

EXAMPLE 2

Synthesis of Octadecyl L-Alanyl

D-Glutamine Hydrochloride (BCH-525)

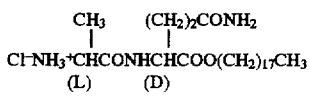

The octadecyl ester of BOC D-glutamine (3.5 g) was prepared by the esterification of BOC D-glutamine (4.4 g, 18 mmole) with octadecanol (5.8 g, 22 mmole) in the presence of carbonyldiimidazole, using the synthetic procedure described in example 1. Removal of the BOC protecting group was undertaken by solubilization of the product in methylene chloride followed by bubbling hydrogen chloride gas through the solution for 10 minutes at room temperature, as described in example 1, to give 2.7 g of the hydrochloride salt of octadecyl D-glutamine.

To the hydrochloride salt of octadecyl D-glutamine (2.2 g, 5 mmole), suspended in 75 mL of chloroform, was added triethylamine (0.8 mL, 5.8 mmole), and this was stirred for a few minutes at ambient temperature. To the reaction was then added BOC L-alanine (1.0 g, 5.5 mmole) and 2-ethoxy-1-ethoxycarbonyl -1,2-dihydrocquinoline (EEDQ; 1.6 g, 6.5 mmole). The reaction was stirred for eighteen hours, at ambient temperature and then extracted with cold 0.5N hydrochloric acid (3×75 mL), 5% sodium bicarbonate (2×75 mL) and water (75 mL). The organic phase was then dried with anhydrous sodium sulphate. Removal of the solvent gave 2.3 g solid. The octadecyl ester of BOC-L-alanyl D-glutamine was purified from this solid by flash silica gel chromatography. The column was eluted with 1:1 hexane/ethyl acetate, 3:1 ethyl acetate/hexane, ethyl acetate, and ethyl acetate/methanol (10% v/v of the latter solvent). Yield of the product was 1.9 g. The product was identified by 300 MHz NMR spectroscopy and TLC. The product could be alternatively purified by crystallization in methylene chloride/ether. Removal of the BOC protecting group was undertaken by solubilization of the product in methylene chloride (filtration was necessary to remove a small amount of insoluble material) followed by bubbling hydrogen chloride gas through the solution for 10 minutes at room temperature. The hazy solution was stored at 4° C. for two hours and filtered, and the solid was dried in vacuo. The yield of white hydrochloride salt of octadecyl L-alanyl D-glutamine was 1.4 g. The final product was confirmed by 300 MHz NMR spectroscopy and TLC.

EXAMPLE 3

Synthesis of Octadecyl D-Alanyl

L-Glutamine Hydrochloride (BCH-527)

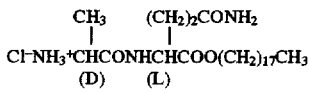

The hydrochloride salt of octadecyl D-alanyl L-glutamine, (1.6 g), was synthesized on the same scale, by the procedure described in example 2. NMR and TLC of the product was identical to the product in example 2.

EXAMPLE 4

Synthesis of α-Octadecyl L-Alanyl

D-Glutamate Hydrochloride (BCH-526)

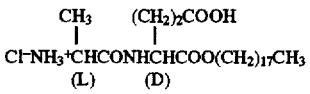

The octadecyl ester of γ-benzyl BOC D-glutamate (7.2 g) was prepared by the esterification of γ-benzyl BOC D-glutamate (4.6 g, 13.5 mmole) with octadecanol (4.4 g, 16.2 mmole) in the presence of carbonyldiimidazole using the synthetic procedure described in example 1. Removal of the BOC protecting group was undertaken by solubilization of the product in ether, followed by extensive bubbling of hydrogen chloride gas through the solution for 3 times for 10 minutes each at room temperature. Storage at 4° C. failed to give a precipitate, and so most of the solvent was removed by rotary evaporation and the concentrate diluted with hexane, again stored at 4° C. for two hours, and the precipitated product collected by filtration. Yield was 5.2 g of the hydrochloride salt of the octadecyl ester of γ-benzyl D-glutamate.

Triethylamine 1.2 mL, 8.7 mmole was added to the hydrochloride salt of octadecyl ester of γ-benzyl D-glutamate (3.9 g, 7.5 mmole), dissolved in 75 mL of chloroform. The mixture was then stirred for a few minutes at ambient temperature. BOC L-alanine (1.6 g, 8.3 mmole) and EEDQ (2.4 g, 9.8 mole) were then added to the reaction. The reaction was stirred for eighteen hours, at ambient temperature and worked up as described in example 2 above, to give crude product (4.9 g) which was used without purification by silica gel chromatography.

Removal of the BOC protecting group was undertaken on a 1.5 g portion of the crude product by solubilization in methylene chloride and extensive bubbling of hydrogen chloride gas, as previously described, to give 1.3 g of the octadecyl γ-benzyl ester of L-alanyl D-glutamate as a gummy solid. The benzyl ester protecting group was removed by dissolving the solid in 75 mL ethanol and stirred at room temperature, overnight, in a hydrogen atmosphere, and in the presence of 300 mg 10% palladium/carbon catalyst. The catalyst was removed by filtration. The solvent was removed by rotary evaporation, and the residue triturated in ether, to give 1.0 g of crude dipeptide. Crystallisation in acetonitrile gave 630 mg of the hydrochloride salt of octadecyl L-alanyl D-glutamate. The final product was confirmed by NMR spectroscopy and TLC.

EXAMPLE 5

Synthesis of γ-Octadecyl L-Alanyl

D-Glutamate Hydrochloride (BCH-524)

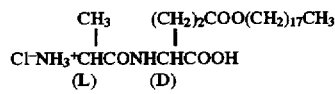

The octadecyl ester of α-benzyl BOC L-alanyl D-glutamate (875 mg) was prepared by the esterification of the α-benzyl ester of BOC L-alanyl D-glutamate (1.8 g, 4.5 mmole) with octadecanol (1.5 g, 5.4 mmole) in the presence of carbonyldiimidazole, using the synthetic procedure described in example 1.

The benzyl ester protecting group was removed by hydrogenolysis, as described in example 4, to give 320 mg of the γ-octadecyl ester of BOC L-alanyl D-glutamate. Removal of the BOC protecting group was undertaken by dissolving the product in methylene chloride, followed by bubbling hydrogen chloride gas through the solution for 10 minutes at room temperature, as described in example 1 to give 140 mg of the hydrochloride salt of γ-octadecyl L-alanyl D-glutamate. The final product was confirmed by NMR spectroscopy and TLC.

EXAMPLE 6

Synthesis of Octadecyl L-Alanyl

D-Isoglutamyl γ-Glycine Hydrochloride (BCH 1315)

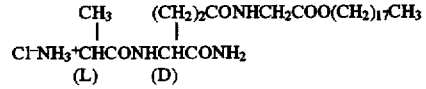

Carbonyldiimidazole (583 mg, 3.6 mmole) was added to BOC L-alanyl D-isoglutamine (955 mg, 3 mmole of the free acid), dissolved in 60 mL dry tetrahydrofuran and stirred under argon flow. The solution was stirred for 45 minutes at room temperature and then octadecyl glycine hydrochloride (1.2, 3.3 mmole) suspended in dry tetrahydrofuran (40 mL) and triethylamine (0.5 mL) was added, to the reaction, under argon flow.

Octadecyl glycine hydrochloride was prepared by the methanesulfonic acid catalyzed esterification of glycine with octadecanol. The suspension was stirred for twenty hours, at room temperature, under argon. Solvent was removed by rotary evaporation and the crude product taken up in methylene chloride and extracted, as described in example 1, above. The octadecyl ester of BOC L-alanyl D-isoglutamyl γ-glycine was purified by crystallization in warm methylene chloride to give 690 mg of product as an off-white solid. The BOC protecting group was removed by reaction with hydrogen chloride gas, as described in example 1. However, no precipitate was formed after storage at 4° C. Therefore, methylene chloride was removed by rotary evaporation, and ether added to the concentrate. Filtration, followed by washing of the solid with ether, gave 450 mg of the hydrochloride salt of octadecyl L-alanyl D-isoglutamyl γ-glycine, as confirmed by NMR spectroscopy and TLC.

EXAMPLE 7

Synthesis of L-Alanyl D-Isoglutamyl Octadecylamine Hydrochloride (BCH-1316)

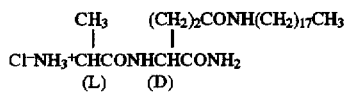

The hydrochloride salt of L-alanyl D-isoglutamyl octadecylamine, 276 mg, was synthesized, on the same scale, by the procedure as described in example 6, except the free base of octadecylamine (890 mg, 3.3 mmole) replaced octadecyl glycine hydrochloride and triethylamine. The final product was confirmed by NMR spectroscopy and TLC.

EXAMPLE 8

Synthesis of Octadecyl L-Valyl

D-Glutamine Hydrochloride (BCH 1317)

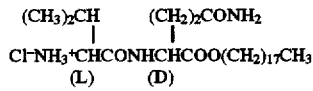

Triethylamine, (0.4 mL, 2.9 mmole) was added, to the hydrochloride salt of octadecyl D-glutamine (synthesis described in example 2 above) (1.1 g, 2.5 mmole) suspended in 50 mL chloroform, and the mix was stirred for a few minutes at room temperature. Then BOC L-valine (0.6 g, 2.8 mmole) and EEDQ (0.8 g, 3.3 mmole) were added. The reactants were stirred for eighteen hours at room temperature and processed as described in example 2. The reaction yielded 1.6 g of crude octadecyl ester of BOC L-valyl D-glutamine which was purified by flash silica gel chromatography. The column was eluted with 2:1 hexane/ethyl acetate, 1:1 hexane/ethyl acetate, and ethyl acetate. However, it was also possible to purify the product by crystallization in methylene chloride and ether. Yield of product was 730 mg. The product was identified by NMR spectroscopy and TLC. Removal of the BOC protecting group was undertaken by dissolving the product in methylene chloride followed by bubbling hydrogen chloride gas through the solution for 10 minutes at room temperature. However, storage of the acid solution at 4° C. for two hours failed to give a precipitate, and so methylene chloride was removed by rotary evaporation. The residue was washed in ether to give, after filtration, 510 mg of the hydrochloride salt of octadecyl L-valyl D-glutamine. The final product was confirmed by 300 MHz NMR spectroscopy and TLC.

EXAMPLE 9

Synthesis of Octadecyl L-Seryl

D-Glutamine Hydrochloride (BCH-1318)

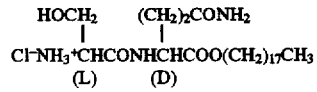

The hydrochloride salt of octadecyl L-seryl D-glutamine, 420 mg, was synthesized, on the same scale, by the procedure described in example 8, except that BOC L-serine (570 mg, 2.8 mmole of the hydrate) replaced BOC L-valine. The final product was confirmed by NMR spectroscopy and TLC.

EXAMPLE 10

Synthesis of Octadecyl L-Threonyl
D-Glutamine Hydrochloride (BCH-1319)

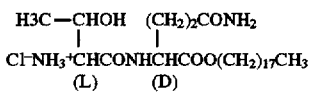

The hydrochloride salt of octadecyl L-threonyl D-glutamine, 410 mg, was synthesized, on the same scale, by the procedure described in example 8, except BOC L-threonine (600 mg, 2.8 mmole) replaced BOC L-valine. The final product was confined by NMR spectroscopy and TLC.

EXAMPLE 11

Synthesis of Octadecyl L-Phenylglycyl
D-Glutamine Hydrochloride (BCK-1320)

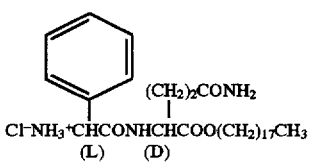

The hydrochloride salt of octadecyl L-phenylglycyl D-glutamine, 750 mg, was synthesized, on the same scale, by the procedure described in example 8, except that BOC L-phenylglycine (700 mg, 2.8 mmole) replaced BOC L-valine. The final product was confirmed by NMR spectroscopy and TLC.

EXAMPLE 12

Synthesis of Octadecyl D-Valyl
L-Glutamine Hydrochloride (BCH-1321)

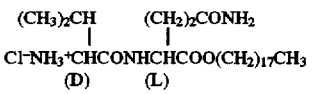

The hydrochloride salt of octadecyl D-valyl L-glutamine, 580 mg, was synthesized, on the same scale, by the procedure described in example 8, except BOC D-valine replaced the L-enantiomer and use was made of the L-enantiomer of glutamine. NMR and TLC of the product was identical to the product produced and described in example 8.

EXAMPLE 3

Synthesis of Octadecyl D-Seryl
L-Glutamine Hydrochloride (BCH-1322)

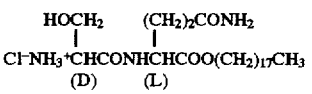

The hydrochloride salt of octadecyl D-seryl L-glutamine, 680 mg, was synthesized, on the same scale, by the procedure described in example 8, above, except BOC D-serine (560 mg, 2.8 mmole) replaced BOC L-valine, and use was made of the L-enantiomer of glutamine. The final product was confirmed by NMR spectroscopy and TLC.

EXAMPLE 14

Synthesis of Octadecyl D-Phenylglycyl
L-Glutamine Hydrochloride. (BCH-1323)

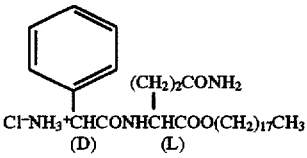

The hydrochloride salt of octadecyl D-phenylglycyl L-glutamine, 800 mg, was synthesized, on the same scale, by the procedure described in example 8, above, except BOC D-phenylglycine (700 mg, 2.8 mmole) replaced BOC L-valine, and use was made of the L-enantiomer of glutamine. The final product was confined by NMR spectroscopy and TLC.

EXAMPLE 15

Synthesis of Octadecyl D-Glutamate
L-Glutamine Hydrochloride (BCH1326)

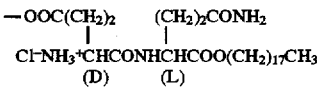

The hydrochloride salt of octadecyl D-glutamate L-glutamine, 800 mg, was synthesized, on the same scale, by the procedure described in example 8, above, except BOC D-glutamate-γ-t-butyl ester (830 mg 2.8 =mole) replaced BOC L-valine, and use was made of the L-enantiomer of glutamine. The final product was confirmed by NMR spectroscopy and TLC.

EXAMPLE 16

Synthesis of Octadecyl D-Ornithyl
L-Glutamate Hydrochloride (BCH-1325)

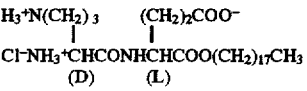

To BOC-L-glutamate-γ-benzyl ester (3.0 g, 12.2 mmoles), dissolved in 100 mL dry tetrahydrofuran and stirring under argon flow was added carbonyldiimidazole (2.0 g, 12.3 mmoles). After stirring for 20 minutes at room temperature, octadecanol (4.0 g, 14.6 mmole) was added, and the reaction was stirred for eighteen hours at room temperature.

Insolubles were removed by filtration. Removal of the solvent by rotary evaporation gave 9.1 g of crude product. The solid was solubilized in 100 mL of methylene chloride and the solution was extracted with 5% hydrochloric acid (2×40 mL), 5% sodium bicarbonate (2×40 mL), and brine (40 mL). The organic phase was then dried with magnesium sulfate. Removal of the solvent gave 5.8 g of solid. The crude product was purified by flash silica gel chromatography. The column was eluted with methylene chloride to give 4.8 g of product.

This product was identified by NMR spectroscopy and TLC. Removal of the BOC protecting group was undertaken by solubilization of the product in ether followed by bubbling hydrogen chloride gas through the solution for 25 minutes at room temperature. The reaction was stirred for one hour at room temperature, and then reduced to approximately half volume by rotary evaporation. The solution was stored at 4° C. for two hours and filtered, and the solid dried in vacuo.

The yield of white hydrochloride salt of the octadecyl ester of γ-benzyl L-glutamate was 2.3 g. The final product was confirmed by NMR spectroscopy and TLC. This product (5.2 mmoles) was added to 50 mL chloroform and triethylamine (0.8 mL, 5.8 mmole), and the reaction mixture was stirred at room temperature for 20 minutes. BOC-N-&-CBZ-D-ornithine (2.0 g, 5.7 mmole) was then added to the reaction mixture, followed by EEDQ (1.4 g, 5.7 mmole). The reaction was stirred for eighteen hours at room temperature, diluted with chloroform, (25 mL), extracted with 5% hydrochloric acid, (2×30 mL), 5% sodium bicarbonate (2×30 mL), brine (30 mL), and dried over magnesium sulphate. The product was crystallized (3:1 ether/methylene chloride) to give 3.4 g of pure compound, which was characterized by NMR spectroscopy and TLC. The benzyl ester protecting group was removed by dissolving the product in 70 mL of ethanol, and stirring overnight, room temperature, in a hydrogen atmosphere, and the presence of 750 mg 10% palladium/carbon catalyst. The catalyst was removed by filtration, and the solvent removed by rotary evaporation to give 2.1 g of the octadecyl ester of BOC D-ornithyl L-glutamate. This product was confirmed by NMR spectroscopy and TLC. Removal of the BOC protecting group was undertaken by dissolving the product in ether, and bubbling hydrogen chloride gas through the solution for 20 minutes at room temperature. The reaction was kept at room temperature for one hour, and then reduced to approximately half volume by rotary evaporation. The cloudy solution was stirred at 4° C. for two hours, filtered, the solid was washed with ether (2×30 mL) and dried in vacuo. This gave 1.7 g of pure octadecyl D-ornithyl L-glutamate hydrochloride, as confirmed by NMR spectroscopy, high resolution mass spectroscopy and TLC.

EXAMPLE 17

Synthesis of Octadecyl L-Tyrosyl Glycyl Glycine Hydrochloride (BCH 276)

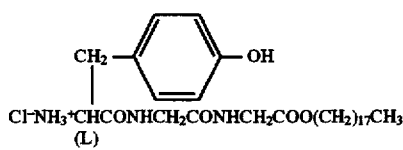

Carbonyldiimidazole (535 mg, 3.3 mmoles) was added to a solution of BOC L-tyrosyl glycyl glycine (1.2 g, 3.0 mmoles) in dry methylene chloride (40 mL) and dry dimethylformamide (10 mL). The solution was stirred under argon for 45 minutes at room temperature, and then octadecanol (976 mg, 3.6 mmole) was added to the reaction. The reaction was stirred under argon, for twenty hours. Solvent was removed by rotary evaporation, and the crude material, 2.5 g, was purified by flash silica gel chromatography. The column was eluted with 4:1 hexane/ethyl acetate, ethyl acetate, and ethyl acetate/methanol (10% v/v of the latter solvent).

Yield of the product as 1.3 g. The product was identified by NMR spectroscopy and TLC. Removal of the BOC protecting group was undertaken by solubilization of the product in methylene chloride followed by bubbling hydrogen chloride gas through the solution for 10 minutes at room temperature. The hazy solution was stored at 4° C. for two hours, and filtered, and the solid dried in vacuo.

The yield of product, octadecyl tyrosyl glycyl glycine hydrochloride, was 950 mg.

EXAMPLE 18

Synthesis of Octadecyl-D-Alanyl-β-Cyanomethyl L-Alanine Hydrochloride (BCH-1365)

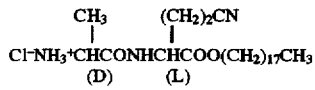

Triethylamine (0.317 mL; 2.28 mmole) was added dropwise to a solution of the octadecyl ester of BOC-D-alanyl L-Glutamine (1 g; 1.75 mmole) in dry tetrahydrofuran (60 ml). The mixture was stirred under a flow of argon for a few minutes after which trifluoroacetic anhydride (0.32 ml; 2.28 mmole) was added over twenty minutes. The reaction was then left at room temperature for eighteen hours. Solvent was removed by rotary evaporation and the crude product taken up in methylene chloride (30 ml). The solution was extracted with 0.5N hydrochloric acid (2×50 ml), 5% sodium bicarbonate (2×50 ml) and brine (2×50 ml). The organic phase was then dried with anhydrous sodium sulfate. The crude, octadecyl ester was purified by flash silica gel chromatography using 2:3 ethyl acetate/hexane as eluent. Yield of the product was 0.66 g; 1.19 mmole; 68% yield. The product was identified by 300 MHz NMR spectroscopy and TLC (Rf=0.4 ethyl acetate/hexane 3:7). The product could be alternatively purified by crystallization in methylene chloride/hexane. Removal of the BOC protecting group was undertaken by dissolving the product (180 mg; 0.326 mmole) in dry ether, followed by bubbling hydrogen chloride gas through the solution for ten minutes at room temperature, as described in example 1 to give 123 mg; 0.25 mmole; 77% yield of the hydrochloride salt of octadecyl-D-alanyl-β-cyanomethyl-L-alanine. The final product was confirmed by NMR spectroscopy, high resolution mass spectra and TLC (Rf=0.48 ehtyl acetate/hexane 3:7).

EXAMPLE 19

Synthesis of Octadecyl-D-Alanyl-ψ [CSNH]-β-Cyanomethyl L-Alanine Hydrochloride (BCH-1375)

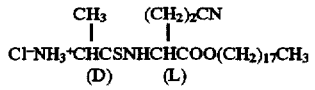

Lawesson's reagent (235 mg; 0.58 mmole) was added to a solution of octadecyl-BOC-D-alanyl-β-cyanomethyl-L-alanine (320 mg; 0.58 mmole) in dry tetrahydrofuran (45 ml) under a flow of argon. The reaction was heated under reflux for 4 hours. Solvent was removed by rotary evaporation and the crude product taken up in methylene chloride (45 ml). The solution was extracted with 5% sodium bicarbonate (3×50 ml); 0.5N hydrochloric acid (2×50 ml) and brien (2×50 ml). The organic layer was then dried with anhydrous sodium sulfate. The crude material was purified by flash silica gel chromatography using 3:7 ethyl acetate/hexane as eluent. Yield of the product was 200 mg; 0.352 mmole; 61% yield. The product was identified by 300 MHz NMR spectroscopy and by TLC (Rf=0.52 ethyl acetate/hexane 3:7).

Removal of the BOC protecting group was undertaken by dissolving the product in dry ether, followed by bubbling hydrogen chloride gas through the solution for 10 minutes at room temperature, as described in example 1 to give 63 mg;

0.125 mmoles; 88% yield of the hydrochloride salt of octadecyl-D-alanyl ψ [CSNH]-β-cyanomethyl-L-alanine. The final product was confirmed by NMR spectroscopy, high resolution mass spectra and TLC (Rf=0.57 10% v/v methanol/ethyl acetate).

EXAMPLE 20

Synthesis of Octadecyl-D-Alanyl ψ [CSNH] L-Glutamine hydrochloride (BCH-1376)

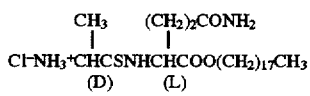

During the work up of the reaction between lawesson's reagent and octadecyl-Boc-D-alanyl-β-cyanomethyl-L-alanine, (60 mg; 0.1 mmole) of octadecyl-BOC-D alanyl ψ [CSNH]-L-glutamine was isolated. This compound was confirmed by NMR spectroscopy and TLC (Rf=0.28 ethyl acetate/hexane 3:2). Removal of the BOC protecting group was undertaken by dissolving the product in dry ether, followed by bubbling hydrogen chloride gas through the solution for 10 minutes at room temperature, as described in example 1 to give 33 mg; 0.063 mmole; 63% yield of the hydrochloride salt of octadecyl-D-alanyl ψ [CSNH]-L-glutamine. The final product was confirmed by NMR spectroscopy; high resolution mass spectra and TLC (Rf=0.54 20% v/v methanol/ethyl acetate). Alternatively, BCH-1376 could be prepared by the hydrolysis of the cyano function of octadecyl-Boc-D-alanyl -ψ-[CSNH]-β-cyanomethyl-L-alanine followed by the deprotection of the BOC group.

EXAMPLE 21

Synthesis of Octadecyl-D-Alanyl L-thioglytamine Hydrochloride (BCH-1373)

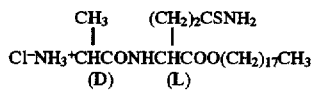

Lawesson's reagent (370 mg; 0.91 mmole) was added to a solution of octadecyl-BOC-D-alanyl-L-glutamine (500 mg; 0.87 mmole) in dry 1,2-dichloro ethane (55 ml) under a stream of argon. The reaction was heated under reflux for 2 hours. Solvent was removed by rotary evaporation and the crude product taken up in methylene chloride (50 ml). The solution was extracted with 5% sodium bicarbonate (3×50 ml); 0.5N hydrochloric acid (2×50 ml) and brine (2×50 ml). The organic layer was then dried with anhydrous sodium sulfate. The crude substance was purified by flash silica gel chromatography using 2:3 ethyl acetate/hexane as eluent. Yield of the product 378 mg; 0.64 mmole; 75% yield. The product was identified by NMR spectroscopy and TLC (Rf=0.34 ethyl acetate/hexane 2:3). Removal of the BOC protecting group was undertaken by dissolving the product in dry ether, followed by bubbling hydrogen chloride gas through the solution for 10 minutes at room temperature, as described in example 1 to give 264 mg; 0.50 mmole; 79% yield of the hydrochloride salt of octadecyl-D-alanyl-L-thioglutamine. The final product was confirmed by NMR spectroscopy, high resolution mass spectra and TLC (Rf= 0.26 20% v/v methanol/ethyl acetate).

EXAMPLE 22

Plaque forming assay

Selected oligopeptide immunomodulators of the invention were tested for immunomodulating activity on antibody producing cells. The testing was done in the following manner.

Outbred CD1 mice were immunized with 0.1% volume for volume sheep red blood cell antigen suspended in saline. The mice were injected intraperitoneally with 0.5 ml, suspension of approximately $2 \times 10^7$ cells.

The mice were injected shortly thereafter with a suspension of an immunomodulator of the invention. The immunomodulator dose was a 0.23 ml of a 1 mg/ml suspension in phosphate buffered saline. The injected dose was 10 mg/kg. The second injection was also intraperitoneal.

The mice were killed five days after injections. Blood samples were taken for analysis of immunoglobulin. The determination was made by enzyme immunoassay using an anti μ-horseradish peroxidase conjugate. The spleen was removed, transferred to a petri dish containing 2 ml of Hank's balanced salt solution and 10 mMolar Hepes buffer (HBSS-HEPES). The spleen was gently crushed by the use of forceps, and the cell suspension was filtered through cotton gauze to eliminate cellular debris. The filtered suspension was brought to volume (5 ml) by the addition of HBSS-HEPES, the cells counted, and the suspension diluted to a final concentration of $5 \times 10^6$ cells/ml.

2 ml of a sheep red blood cell solution were transferred to 15 ml centrifuge tubes, and washed three times with HBSS-HEPES by centrifugation for ten minutes (low speed). The final pellet was diluted 1 to 8 with HBSS-HEPES.

Prior to use, guinea pig complement was reconstituted according to the manufacturer's instructions (Cedarlane, Hornby, Ontario) and diluted 1 to 20 with HBSS-HEPES.

The assay was done by preparing a mixture of 550 μl complement (1/20), 77 μl solution of sheep red blood cells (1/8 dilution) and 33 μl of a solution of spleen cells ($5 \times 10^6$/ml) to a total volume of 660 μl. 200 μl of this mixture was placed into a Cunningham chamber formed by two glass microscope slides. The slides were sealed with melted wax plus petroleum jelly, and the chambers (duplicate samples) were incubated for forty-five minutes at 37° C. The areas of hemolysis were counted. Haemolysis is indicative of antibody forming cells, and they are referred to as plague-forming cells (PFC). The results are recorded as PFC per $10^6$ spleen cells. The results are summarized in Table 1.

EXAMPLE 23

Natural killer cells activity

Three week-old $C_{57}BL/6$ mice were procured and quarantined for 24 to 48 hours prior to treatment. The five oligopeptides described in tables 2, 3 and 4 were admixed with a 0.4% water solution of carboxymethylcellulose. The solutions were stored at 4° C. until use. Ribavarin (1-β-D-ribofuranosyl-1,2,4-triazole-carboxamide) was used in each subsequent experiment as a control.

Animals were treated with a 50 mg/kg/day dosage of one of the tested compound and were killed 24 hr after the final treatment and their spleens removed. Each spleen was suspended in RPMI-1640 medium and homogenized using a stomacher (Tekmar, Cincinnati, Ohio). Red blood cells were removed by haemolytic lysis. Remaining splenocytes were washed three times in RPMI-1640 and resuspended in medium containing 20% fetal calf serum and counted using a Coulter counter (Hialeah, Fla.) before use in natural killer (NK) and macrophage function assays and T and B cell enumeration studies.

Natural killer (NK) activity of murine cells was determined by testing splenic cells for their ability to lyse YAC-1 tumor cells in a conventional 4 hr chromium release assay as an indicator of NK was expressed as: % chromium release= (experimental counts per minute (cpm)–background cpm)/ (maximum cpm-background cpm)

Results are shown in Table 3 infra.

Generally all the tested immunomodulators, of the invention, were well tolerated by the animals.

The NK cells activity of splenocytes taken from mice treated with the BCH compounds is summarized in Table 3. Only BCH-527 appeared to significantly stimulate this activity; a similar effect was seen at both effector: target cell ratios. BCH-524 and 525 were marginally suppressive to the NK cell activity in the experiment. The stimulation seen with BCH-527 compares well with the stimulation seen with two other immunomodulators, namely 7-thia-8-oxoguanosine and Aviron (ImuVert).

EXAMPLE 24

Macrophage activation and T/B cells assay

The murine cells of interest were obtained using the method described in Example 22.

Macrophage function was assessed by an interleukin-1 (IL-1) assay that utilizes responsiveness of mouse thymocytes to phytohemagglutin (PHA) which is dependent on IL-1 for its reactivity.

Murine thymocytes in a concentration of $10^7$ cells/ml were suspended in RPMI 1640 medium containing 2% PHA, 5% fetal bovine serum, and 0.05 mM 2-mercaptoethanol/penicillin-streptomycin. A total of 100 µl of this suspension was added to each well of a 96-well flat-bottomed microplate containing serial dilutions of superhate to be assayed for IL-1. The cells were incubated 72 hr at 37° C. During the last 4 hr of the incubation, the cells were pulsed with [$^3$H] thymidine (1 µCi/well). The cells were then harvested and [H$^3$] thymidine incorporation was determined using a direct counter.

The effect of the inventive immunomodulators on macrophage function is seen in Table 2. It is expressed by IL-1 activity in splenocytes from the treated mice. A considerable variation occurred in most treatment groups. Compounds BCH-523, 524 and 527 are somewhat stimulatory, whereas BCH-525 and 526 are moderately inhibitory.

Splenic cells were enumerated with the following assay. Dispersed splenocytes were reacted with fluorescein isothiocyanate-labelled murine monoclonal antibody anti-Ly5 for B cell enumeration and phycoerythrin-labelled monoclonal antibody anti-Thy 1.2 for T cell counts. The labelled cells were then enumerated with a fluorescence-activated cell sorter (FACS) (EPICS-C, Coulter Corp., Hialeah, Fla.).

The splenic T and B cell enumeration data obtained using these BCH compounds are shown in Table 4. BCH-526 and 527 appeared to increase % B cells while suppressing T cells. BCH-524 appeared suppressive both to T and B cells.

EXAMPLE 25

Natural killer cells activity and macrophage activation

The 14–16g female and male Balb/c mice were obtained from Simonsen Laboratories (Gilroy Calif.). They were quarantined 24 hours prior to use, and maintained on Wayne Lab Blox and tap water. Mice that were infected, were infected intranasally with influenza virus. The influenza A/NWS/33 (H1N1) virus was obtained from Dr. K. W. Cochran of the University of Michigan (Ann Arbor, Mich.). A virus pool was prepared by infecting confluent monolayers of Madin Darby canine kidney (MDCK) cells, incubating them at 37° C. in 5% $CO_2$, and harvesting the cells at 3 to 5 days when the viral cytopathic effect was 90 to 100%. The virus stock was ampuled and stored at −80° C. until used. Once infected the mice were drinking water containing 0.006% of oxytetracycline (Pfizer, New York, N.Y.) to control possible secondary bacterial infections.

Octadecyl L-alanyl D-glutamine (BCH-527) was suspended in a sterile 0.4% carboxymethylcellulose (CMC) solution for intraperitoneal (i.p.) treatment into mice. Octadecyl L-alanyl D-glutamine (BCH-527) was used at doses of 200, 100, and 50 mg/kg/day, administered once daily on days −1, +1,+3, +5, and +7 relative to virus treatment (injection #1, #2, #3, #4 and #5 respectively).

Natural killer cells activity and macrophage function were determined in spleens of 5 mice 24 hours after the first treatment, at each drug dosage and in normal controls. Similar assays were also done after the day 5 treatment in 5 infected and 5 uninfected mice, treated with each dosage and from similar numbers of virus and normal controls.

Natural killer cells activity was determined as described in example 23. Ratios of splenic cells to tumor cells used were 5:1, 25:1, 50:1, and 100:1.

Macrophage function was assayed by an interleukin-1 (IL-1) determination that utilises an ELISA kit (Genzyme Corp., Cambridge, Mass.) for murine IL-1. Splenic monocytes were incubated for 24 hours in 20 µg/mL of lipopolysaccharide. The supernates were removed and analysed by ELISA.

The results are summarized in tables 5–6.

An important immunomodulatory effect of octadecyl L-alanyl D-glutamine (BCH-527) in the infected and uninfected mice was observable. As seen in table 5, after 4 injections with octadecyl L-alanyl D-glutamine (BCH-527) at doses of 100 and 50 mg/kg/day, a strong activation of NK cells was seen especially in infected mice.

Octadecyl L-alanyl D-glutamine (BCH-527) was also a significant macrophage activator as seen in table 6. That was especially apparent after 4 treatments, and was manifested most strongly in the influenza virus-infected animals.

EXAMPLE 26

Antiviral activity

Swiss Webster female mice (Simonson Labs, Gilroy, Calif.) weighting ~12 gr. each at the beginning of the experiment were infected i.p with murinecytomegalovirus (MCMV) (Smith strain). The virus had been pretitrated in mice to kill 80–90% of the animals, although there is variation in mortality from experiment to experiment, the virus killed only 55% of placebo control animal. Octadecyl D-alanyl L-glutamine (BCH-527) was administered once daily on days −1, +1, +3, +5, and +7 relative to virus treatment. BCH-527 was suspended in a sterile 0.4% carboxymethylcellulose solution. Doses varying from 50 mg/kg to 200 mg/kg were injected i.p. to the animals. The placebo control, 0.4% carboxymethylcellulose, was administered at the same time.

Ganciclovir was given once daily for 5 days starting 24 hours after virus inoculation. A dose of 25 mg/kg in a sterile solution of physiological saline solution was injected i.p route.

Death were recorded daily for 21 days, the mean day of calculation took into account mice that died. Tissue virus titres were made by titration of virus obtained from 10% tissue homogenates. These titration were conducted in C127I cells in 96 well plates (Smee, D. F., A. Colletti, H. A. Alaghamandan, and L. B. Allen. 1989. Evaluation of continuous cell lines in antiviral studies with murinecytomegalovirus. Arch. Virol. 107:253–260). Calculation of virus titer was made by the 50% endpoint dilution method (Reed, L. J. and M. Muench. 1938. A simple method of estimating 50% endpoints. Am. J. Hyg. 27: 493–498). The results as shown in tables 7 and 8, indicate that the immunomodulator octadecyl L-alanyl D-glutamine (BCH-527) at three doses, prevented death and reduced MCMV tissue virus titres in mice.

Toxicity controls

Groups of 5 uninfected mice were treated the same way and at the same times as described above. These animal were checked daily for survival. Their weigths were taken before the first treatment and 24 hours after the last treatment to determine drug effect on weight gain. The results are showed in table 9.

Statistical interpretations

Survival (Chisquare with Yate's correction), mean day to death (Student's test) and virus titer (Student's test) were made by two tailed analyses.

TABLE 1

Effect of Candidate Immunomodulators on Antibody Production against SRBC Antigen, as Determined by Plaque Assay and Enzyme Immunoassay

| Experiment Number[A] | Candidate Immunomodulator[B] | Plaque Assay[C] | Enzyme Immunoassay[D] |
|---|---|---|---|
| 1 | Saline (control) | 467 ± 93 (100%) | 100% |
| 1 | BCH-523 | 1186 ± 323 (254%) | 171% |
| 2 | Saline (control) | 358 ± 298 (100%) | 100% |
| 2 | BCH-523 | 877 ± 220 (245%) | 138% |
| 3 | Saline (control) | 410 ± 382 (100%) | 100% |
| 3 | BCH-523 | 826 ± 291 (201%) | 261% |
| 4 | Saline (control) | 363 ± 396 (100%) | 100% |
| 4 | BCH-523 | 682 ± 246 (188%) | 160% |
| 5 | Saline (control) | 423 ± 365 (100%) | 100% |
| 5 | BCH-524 | 245 ± 90 (58%) | 80% |
| 5 | BCH-526 | 325 ± 300 (77%) | 82% |
| 6 | Saline (control) | 565 ± 280 (100%) | 100% |
| 6 | BCH-525 | 1073 ± 234 (190%) | 161% |
| 7 | Saline (control) | 7 ± 5 (100%) | 100% |
| 7 | BCH-527 | 479 ± 322 (6843%) | 523% |
| 7 | BCH-523 | 385 ± 33 (5500%) | 465% |
| 8 | Saline (control) | 496 ± 272 (100%) | 100% |
| 8 | BCH-1315 | 1012 ± 207 (204%) | 202% |
| 8 | BCH-1316 | 759 ± 252 (153%) | 186% |
| 9 | Saline | 504 ± 407 (100%) | 100% |
| 9 | BCH 1317 | 750 ± 191 (149%) | 189% |
| 9 | BCH 1318 | 613 ± 166 (122%) | 121% |
| 9 | BCH 1325 | 150 ± 110 (30%) | 60% |
| 10 | Saline | 794 ± 394 (100%) | 100% |
| 10 | BCH 1325 | 456 ± 261 (57%) | 67% |
| 11 | Saline | 187 ± 139 (100%) | 100% |
| 11 | BCH-276 | 439 ± 305 (235%) | 160% |

[A]Experiments show the immunomodulator effect of BCH 523 is observed in different mice.
Experiment 1 and 2; inbred C3H mouse.
Experiment 3 and 4; outbred CD1 and CF1 mouse.
[B]BCH numbers refer to candidate immunomodulators
523; octadecyl L-alanyl D-isoglutamine
524; γ-octadecyl L-alanyl D-glutamate
526; α-octadecyl L-alanyl D-glutamate
525; octadecyl L-alanyl D-glutamine
527; octadecyl D-alanyl L-glutamine
1315; octadecyl L-alanyl D-glutamyl glycine
1316; L-alanyl D-isoglutamyl octadecylamine
[C]PFC per 10[6] spleen cells. Percentage refers to increase (decrease) in PFC relative to control (100%).
[D]Percentage refers to increase (decrease) in IgM antibody, as measured by absorbance, relative to control (100%).
Number of mice per group for evaluation of immunomodulators was seven for the control group, and six for the treated group.

TABLE 2[a]

Effect of oligopeptide immunomodulators on Macrophage Function[b] in C57BL/6 Mice

| Compound | Dosage mg/kg/day | Mean CPM of Treated Thymocytes ± SD[c] |
|---|---|---|
| BCH-523; octadecyl L-alanyl D-isoglutamine | 50 | 5236 ± 320 |
| BCH-524; γ-octadecyl L-alanyl D-glutamate | 50 | 5491 ± 1269 |
| BCH-525; octadecyl L-alanyl D-glutamine | 50 | 3392 ± 201 |
| BCH-526; α-octadecyl L-alanyl D-glutamate | 50 | 3413 ± 206 |
| BCH-527; octadecyl D-alanyl L-glutamine | 50 | 5660 ± 1011 |
| Normal Controls | 0 | 4791 ± 426 |

[a]all compounds administered i.p. every other day for 4 injections; splenocytes taken 24 hr after final treatment for assay.
[b]Macrophage function expressed as IL-1 activity in splenocytes, measured by [³H]thymidine uptake in IL-1-dependent PHA-stimulated thymocytes.
[c]Standard deviation (n = 5).

TABLE 3[a]

Effect of oligopeptide immunomodulators on
Natural Killer Cell Activity[b] in C57BL/6 Mice

| Compound | Dosage (mg/kg/day) | % Chromium Release ± SD[c] Effector:Target Ratio 50:1 | Effector:Target Ratio 25:1 |
|---|---|---|---|
| BCH-523; octadecyl L-alanyl D-isoglutamine | 50 | 15.2 ± 2.3 | 10.6 ± 1.5 |
| BCH-524; γ-octadecyl L-alanyl D-glutamate | 50 | 14.3 ± 1.9 | 9.8 ± 3.6 |
| BCH-525; octadecyl L-alanyl D-glutamine | 50 | 13.9 ± 1.2 | 7.2 ± 2.3 |
| BCH-526; α-octadecyl L-alanyl D-glutamate | 50 | 17.2 ± 3.3 | 12.8 ± 2.1 |
| BCH-527; octadecyl D-alanyl L-glutamine | 50 | 24.0 ± 1.7 | 13.9 ± 2.0 |
| Normal Controls | 0 | 19.5 ± 3.9 | 11.6 ± 1.8 |

[a] all compounds administered i.p. every other day for 4 injections; splenocytes taken 24 hr after final treatment for assay.
[b] NK cell activity expressed as % chromium release in YAC-1 tumor cells lysed by splenocytes (2).
[c] Standard deviation (n = 5).

TABLE 4[a]

Effect of oligopeptide immunomodulators on
Total T and B Cells in Splenocytes[b] in C57BL/6 Mice

| Compound | Dosage (mg/kg/day) | % Cells/Spleen ± SD[c] T Cells | B Cells |
|---|---|---|---|
| BCH-523; octadecyl L-alanyl D-isoglutamine | 50 | 49 ± 7.7 | 39 ± 9.3 |
| BCH-524; γ-octadecyl L-alanyl D-glutamate | 50 | 35 ± 9.6 | 33 ± 10.2 |
| BCH-525; octadecyl L-alanyl D-glutamine | 50 | 53 ± 9.5 | 34 ± 10.6 |
| BCH-526; α-octadecyl L-alanyl D-glutamate | 50 | 40 ± 2.4 | 43 ± 1.4 |
| BCH-527; octadecyl D-alanyl L-glutamine | 50 | 39 ± 2.3 | 43 ± 1.5 |
| Normal Controls | 0 | 49 ± 3.9 | 37 ± 2.7 |

[a] all compounds administered i.p. every other day for 4 injections; splenocytes taken 24 hr after final treatment for assay.
[b] Cell enumeration performed by FACS analysis using monoclonal antibodies anti-Thy 1.2 for T cells, anti-Ly5 for B cells.
[c] Standard deviation (n = 5).

TABLE 5

Effect of i.p. BCH-527 Treatment on Natural Killer Cell
Activity in Normal and Influenza Virus-Infected BALB/c Mice.

| Treatment group | Dosage (mg/kg/day) | Mean Release (2SE)* at Effector:Target Cell Ratio 100:1 | 50:1 | 25:1 | 12:1 |
|---|---|---|---|---|---|
| | | Uninfected-24 hr post-injection #1 | | | |
| BCH-527 | 200 | 20.4(2.4) | 17.3(1.4) | 11.3(0.6) | 6.6(0.6) |
| | 100 | 20.0(2.0) | 16.6(1.9) | 10.6(1.8) | 5.9(1.6) |
| | 50 | 21.2(2.9) | 17.6(1.1) | 10.8(1.3) | 6.1(1.2) |
| | 0 | 21.5(3.8) | 18.3(0.6) | 12.0(1.4) | 7.2(1.3) |
| | | Uninfected-24 hr post-injection #4 | | | |
| BCH-527 | 200 | 18.2(1.0)* | 12.8(0.7)** | 8.6(0.6)* | 1.1(0.5)** |
| | 100 | 22.3(2.0) | 16.4(1.8) | 11.8(1.7) | 3.6(1.4) |
| | 50 | 23.3(1.0)** | 17.1(0.6)** | 12.7(0.4)** | 4.3(0.3)** |
| | 0 | 20.0(1.1) | 14.5(0.5) | 9.8(0.6) | 2.2(0.4) |
| | | Infected-24 hr post-injection #4 | | | |
| BCH-527 | 200 | 17.6(1.1) | 12.9(0.9) | 9.6(0.9) | 7.3(0.3)** |
| | 100 | 26.5(1.6)** | 20.8(1.4)** | 16.9(1.3)** | 12.1(1.2)** |
| | 50 | 23.9(1.1)** | 18.5(1.0)** | 14.8(0.9)** | 10.3(0.8)** |
| | 0 | 16.6(2.3) | 13.1(2.1) | 7.5(1.8) | 3.2(1.6) |

*Mean percent chromium release (2 standard error) at effector:target cell ratios indicated. n = 5
*P < 0.05, **P < 0.01

TABLE 6

Effect of BCH-527 on macrophage Activation[a] in Normal and Influenza Virus Infected BALB/c Mice.

| BCH-527 Dose (mg/kg/day) | IL-1 Conc. (µg/ml) (2SE) | | |
|---|---|---|---|
| | Uninfected 24 hr Post-injection #1 | Uninfected 24 hr Post-injection #4 | Infected 24 hr Post-injection #4 |
| 200 | 16.6(3.7)** | 31.4(3.4)* | 29.1(7.4)** |
| 100 | 32.6(2.7) | 40.7(8.2)** | 179.3(27.0)** |
| 50 | 34.5(3.0) | 21.2(3.3)* | 46.4(6.4)** |
| 0 | 33.9(5.0) | 26.5(5.1) | 9.1(1.6) |

[a]Expressed as IL-1 concentration, n = 5
*P < 0.05, **P < 0.01.

TABLE 7

Effects of BCH-527 and ganciclovir on mortality in MCMV-infected mice.

| Compound | Dose (mg/kg) | Survivors/ total (%) | Mean day to death[a] |
|---|---|---|---|
| BCH-527 | 50 | 9/10 (90)* | 4.0 ± 0.0 |
| BCH-527 | 100 | 7/9 (78)* | 10.5 ± 6.3 |
| BCH-527 | 200 | 10/10 (100)** | >21** |
| Ganciclovir | 25 | 10/10 (100)** | >21** |
| Placebo | — | 9/20 (45) | 6.5 ± 2.5 |

[a]Of mice that died on or before day 21 of the infection
*P < 0.05, **P < 0.01.

TABLE 8

Effects of BCH-527 and ganciclovir on MCMV titers in tissues after 3 and 6 days.

| Compound | Dose (mg/kg) | Virus titer (Log₁₀CCID₅₀[1]/gram) in | | | |
|---|---|---|---|---|---|
| | | Liver | Lung | spleen | salivary gland |
| Day 3 results | | | | | |
| BCH-527 | 50 | 3.1±0.7* | <2.5±0.0 | 6.1±0.6 | 3.0/0.4 |
| BCH-527 | 100 | 2.9±0.7** | <2.5±0.0 | 4.7±1.6 | 3.0±0.4 |
| BCH-527 | 200 | 2.9±0.4** | <2.5±0.0 | 5.3±0.4* | <2.5±0.0 |
| Ganciclovir | 25 | 2.6±0.2** | <2.5±0.0 | 5.7±0.3 | 3.1±0.6 |
| Placebo | — | 4.7±0.3 | 3.1±0.7 | 6.3±0.6 | <2.5±0.0 |
| Day 6 results | | | | | |
| BCH-527 | 50 | 3.1±1.1 | 3.4±0.6 | 4.3±1.2 | 2.7/0.1* |
| BCH-527 | 100 | <2.5±0.0 | 3.9±0.8 | 4.9±0.6 | 2.8±0.3* |
| BCH-527 | 200 | <2.5±0.0 | 3.1±0.4 | 3.7±0.7 | 3.5±0.7 |
| Ganciclovir | 25 | 3.3±0.8 | 3.5±0.6 | 3.6±0.9 | 3.3±0.8 |
| Placebo | — | 3.3±1.5 | 4.7±1.2 | 4.2±1.4 | 4.2±1.3 |

[1]: cell culture infected dose
*P < 0.05, **P < 0.01

TABLE 9

Effects of BCH-527 and ganciclovir on mortality and weight gain in uninfected mice.

| Compound | Dose (mg/kg) | Survivors/ total (%) | Mean Weight Gain (gm)[b] |
|---|---|---|---|
| BCH-527 | 50 | 5/5 (100) | 8.4 |
| BCH-527 | 100 | 5/5 (100) | 9.0 |
| BCH-527 | 200 | 5/5 (100) | 6.9 |

TABLE 9-continued

Effects of BCH-527 and ganciclovir on mortality and weight gain in uninfected mice.

| Compound | Dose (mg/kg) | Survivors/ total (%) | Mean Weight Gain (gm)[b] |
|---|---|---|---|
| Ganciclovir | 25 | 5/5 (100) | 9.5 |
| Placebo | — | 5/5 (100) | 9.2 |

[b]Difference between initial weight at start of treatment and weight 24 hours after the final treatment.

We claim:

1. An oligopeptide of formula (II):

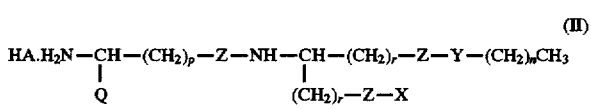

(II)

wherein:

p is an integer selected from zero to four;

each Z is independently C=O or C=S;

each r is independently an integer selected from zero to two;

Y is selected from the group consisting of —O—, —S— and —NH—;

n is an integer selected from eleven to nineteen;

X is $NH_2$, OH or $OCH_3$;

HA, if present, is an organic or inorganic acid which will form a physiologically acceptable salt with said oligopeptide; and Q is $C_1$-$C_4$ branched or unbranched alkyl, phenyl, benzyl, hydroxymethyl or a side chain from any naturally occurring amino acid.

2. The oligopeptide according to claim 1, wherein Z is C=O, Y is —O— or —NH—, n is 17, and X is $NH_2$ or OH.

3. The oligopeptide according to claim 1, of formula (III):

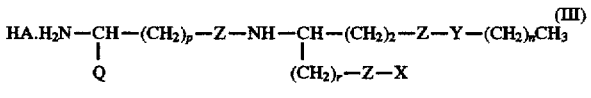

(III)

wherein:

p is an integer selected from zero to four;

each Z is independently C=O or C=S;

r is an integer selected from zero to two;

Y is selected from the group consisting of —O—, —S— and —NH—;

n is an integer selected from eleven to nineteen;

X is $NH_2$, OH or $OCH_3$;

HA, if present, is an organic or inorganic acid which will form a physiologically acceptable salt with said oligopeptide; and Q is $C_1$-$C_4$ branched or unbranched alkyl, phenyl, benzyl, hydroxymethyl or a side chain from any naturally occurring amino acid.

4. The oligopeptide according to claim 3, wherein Z is C=O, Y is —O— or —NH—, X is $NH_2$ or OH, and n is 17.

5. The oligopeptide according to claim 3, wherein r is 1.

6. The oligopeptide according to claim 3 selected from the group consisting of octadecyl L-alanyl D-isoglutamine, γ-octadecyl L-alanyl D-glutamate, octadecyl L-alanyl D-glutamine, α-octadecyl L-alanyl D-glutamate, octadecyl D-alanyl L-glutamine, octadecyl L-phenylglycyl D-glutamine, octadecyl D-valyl L-glutamine, octadecyl D-seryl L-glutamine, octadecyl D-phenylglycyl L-glutamine, octadecyl D-glutamate L-glutamine, octadecyl D-ornithyl L-glutamate, octadecyl L-tyrosyl glycyl glycine, octadecyl D-alanyl-β-cyanomethyl L-alanine, octadecyl D-alanyl-ψ[CSNH]-β-cyanomethyl L-alanine, octadecyl D-alanyl-ψ[CSNH] L-glutamine, octadecyl D-alanyl L-thioglutamine, and any pharmaceutically acceptable acid addition salt thereof.

7. The oligopeptide according to claim 3 selected from the group consisting of octadecyl L-alanyl D-isoglutamyl γ-glycine, L-alanyl D-isoglutamyl octadecylamine, octadecyl L-valyl D-glutamine, octadecyl L-seryl D-glutamine, octadecyl L-threonyl D-glutamine, and any pharmaceutically acceptable acid addition salt thereof.

8. The oligopeptide according to claim 1, of formula (IV):

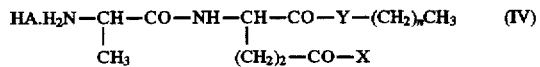

wherein:

Y is selected from the group consisting of —O—, —S— and —NH—;

n is an integer selected from eleven to nineteen;

X is $NH_2$, OH or $OCH_3$; and

HA, if present, is an organic or inorganic acid which will form a physiologically acceptable salt with said oligopeptide.

9. The oligopeptide octadecyl D-alanyl L-glutamine.

10. A pharmaceutical composition comprising at least one compound according to claim 1, 3, or 8 in an amount effective to produce an immunomodulating activity, and a pharmaceutically acceptable carrier.

11. The pharmaceutical composition according to claim 10, additionally comprising an antiviral, antimicrobial, or anticancer compound.

12. The pharmaceutical composition according to claim 11, wherein said antiviral compound is selected from the group consisting of acyclovir, ganciclovir, ribavirin, amantidine, azidothymidine, foscarnet, 2'-deoxy-3'-thiacytidine (3TC), 2'3'-dideoxycytidine (ddC), 2'3'-dideoxyinosine (ddI), 2'3'-dideoxyadenosine (ddA), 5'-iododeoxyuridine, and Carbovir.

13. A method for the treatment or prophylaxis of a viral infection in a mammal, comprising the step of administering an antiviral dose of a pharmaceutical composition according to claim 10.

14. The method according to claim 13, wherein said viral infection is selected from the group consisting of CMV and influenza infections.

* * * * *